United States Patent [19]

Kreisher

[11] Patent Number: 4,589,965
[45] Date of Patent: May 20, 1986

[54] METHOD FOR ELECTROBLOTTING

[75] Inventor: John H. Kreisher, Ridgefield, Conn.

[73] Assignee: International Biotechnologies, Inc., New Haven, Conn.

[21] Appl. No.: 671,475

[22] Filed: Nov. 14, 1984

[51] Int. Cl.[4] ............................................. G01N 27/28
[52] U.S. Cl. ............................... 204/182.8; 204/299 R
[58] Field of Search ........... 204/180 G, 180 R, 299 R, 204/301, 180 S, 182.8, 182.7, 180.1

[56] References Cited

FOREIGN PATENT DOCUMENTS 8102790 10/1981 PCT Int'l Appl. .

OTHER PUBLICATIONS

Bittner, M. et al., "Electrophoretic Transfer of Proteins and Nucleic Acids from Slab Gels to Diazobenzyloxymethyl Cellulose or Nitrocellulose Sheets", *Analytical Biochemistry* vol. 102, pp. 459–471, (1980).

Gibson, W., "Protease-Facilitated Transfer of High--Molecular-Weight Proteins During Electrotransfer to Nitrocellulose", *Analytical Biochemistry*, vol. 118, pp. 1-3, (1981).

Towbin, H. et al., "Electrophoretic Transfer of Proteins from Polyacrylamide Gels to Nitrocellulose Sheets: Procedure and Some Applications", *Proc. of National Acadamy of Sciences*, USA, vol. 76, pp. 4350–4354, (1979).

*Primary Examiner*—John F. Niebling
*Assistant Examiner*—B. J. Boggs, Jr.
*Attorney, Agent, or Firm*—Bachman & LaPointe

[57] ABSTRACT

A rapid and effective method for electroblotting is provided whereby an electrophoretically resolved material in a gelatin sheet is quickly and efficiently transferred to a membrane with high pattern definition and resolution.

12 Claims, No Drawings

METHOD FOR ELECTROBLOTTING

BACKGROUND OF THE INVENTION

Electrophoresis, in general, is the phenomenon of the migration of charged particles or ions in a liquid carrier medium under the influence of an electric field. This phenomenon can be used to separate small particles which, by reasons of different surface chemical properties, exhibit different concentrations of surface charge in the given medium. Under the influence of the electrical field, the electrophoretic mobilities of the various classes of charged particles in the carrier medium will be different. A sample introduced at some point into the sheet of liquid carrier medium (buffer) diffuses slowly in a narrow band in the absence of a potential gradient; however, when the potential gradient is applied to the sheet of buffer, the sample particles are separated under the influence of the electrical field into various particle groups or components depending upon the electrophoretic mobility of the respective particles, the strength of the field, and the length of time that the particles remain in the field. Particles of similar mobility are concentrated in distinctive zones or bands at defined distances from the point of sample introduction (origin).

Blotting or transfer of electrophoretically resolved material, such as DNA, RNA, and protein, has become a standard procedure when sensitive and specific detection of biologically interesting macromolecules is required.

Electroblotting offers significant advantages over capillary blotting in that the electroblotting procedure is much quicker. Capillary transfer and electroblotting both require that the gel be placed in contact with the paper or other membrane to which the proteins or nucleic acids or other materials will be transferred. The difference between the methods is the transfer driving force. In capillary transfer the driving force is the absorptive potential of the filter paper, or other material. The transfer material, e.g., nitrocellulose or nylon, is placed between the gel and the absorptive paper. In electroblotting, however, as currently practiced the gel and transfer material are vertically suspended in a buffer tank between two electrodes. The protein or nucleic acids are thus driven out of the gel onto the transfer material using electrical potential. For example, a typical system involves placing a nylon membrane against a gelatin sheet, submerging the gel-nylon assembly vertically into a buffer solution, then applying an electric potential transversely across the assembly using the buffer solution as the conducting medium. This system typically uses two platinum wire electrodes, one on each side of a gel-nylon combination, and establishes a voltage gradient in the buffer solution. The electrodes are laid out in grid fashion and spaced at a distance from the gel and nylon to obtain a reasonably uniform electric field using the least amount of platinum.

The blotting procedure offers significant advantages. Firstly, molecules in the matrix of a gel are relatively inaccessible to probes such as antibodies. Transfer to the surface of a membrane allows analyses that are difficult or impossible in the gel. Also, since the transferred molecules are located at or near the surface of the membrane, analysis time is substantially reduced. In addition, the membranes are relatively strong and easy to handle in contrast to the gels which are easily torn. Moreover, the transferred molecules are bound to the membrane so that there is no loss of resolution while biological activity is usually retained. Thus, storage of the membrane prior to use is usually feasible.

However, electroblotting as currently practiced suffers from significant disadvantages. The electric field at the gel and nylon surfaces tends to be non-uniform and there tends to be voltage leakage around the gel-nylon assembly. The oxygen and hydrogen bubbles which are generated at the electrodes tend to impede electric current flow through the buffer solution if the electroblot is conducted in a horizontal manner. The physical supports required for the vertically suspended gel further reduce electric current flow and contribute to non-uniformity of field. The cost of platinum for the electrodes precludes its optimum usage and adds significantly to the overall cost of the equipment. A particularly troublesome disadvantage of this procedure is that it is inherently slow. Four hours of running time at 80 volts is typical.

Therefore, it is a principal object of the present invention to provide a rapid and efficient method for electroblotting.

It is a further object of the present invention to provide a method as aforesaid which eliminates the necessity for platinum electrodes.

It is an additional object of the present invention to provide a method as aforesaid which obtains high resolution and absence of diffusion.

Further objects and advantages of the present invention will appear hereinbelow.

SUMMARY OF THE INVENTION

In accordance with the process of the present invention the foregoing objects and advantages are readily obtained. In accordance with the process of the present invention, an electrophoretically resolved material is provided in a gelatin sheet, said sheet is placed in contacting relationship with an immobilizing material, for example, paper, a membrane, nylon etc., sandwiching said sheet-material combination between two plate electrodes, preferably but not necessarily in direct contacting relationship, to form an assembly, and applying electric current to said electrodes.

Preferably, the assembly is disposed in a horizontal relationship which is an advantage with fragile gels in handling and operation. While a conductive buffer solution may be used if desired, it is not necessary; however, preferably a small amount of buffer is placed between the electrodes and sheet-material combination to insure good conductance.

The process of the present invention offers significant advantages over the procedure used heretofore. Firstly, as indicated hereinabove, the assembly may be horizontally disposed which is easier to use than a vertical disposition. Significantly, the process of the present invention is efficient, extremely rapid and inexpensive to manufacture. Thus, depending upon variables such as voltage, current, etc., good electroblot patterns can be transferred to the receptor in as short a period as one second or less using under 30 volts. This compares with four hours or more at 80 volts using conventional electroblotting systems and represents an order of magnitude improvement which is surprising and unexpected and greatly significant in its consequences. Moreover, because of the short exposure time heating of the gel is minimal and no visible gas bubbles are generated at the electrodes during the ultra-short exposures. Further, the present invention contemplates a means of bubble disposal without inhibiting electrical current during longer runs.

Additional advantages of the present invention include the fact that two, flat electrically conductive plates are used as electrodes eliminating the need for expensive platinum wire, and that a buffer solution bath is not necessary. The process of the present invention is an extremely efficient and inexpensive procedure and obtains superior pattern definition and resolution in a low voltage operation, all of which are particularly surprising in view of the rapidity of the process. Also, when a voltage is applied to the electrodes the resultant electric field is extremely uniform and of high current capability. In addition, the process of the present invention makes the use of disposable electrodes feasible. Although the instant process is particularly advantageous for electroblotting, it is readily applicable to other electrophoresis processes and has application to any molecular transfer process that is enhanced by an electric field.

Thus, it can be readily seen that the process of the present invention is surprising in the scope of its advantages and indeed is of revolutionary impact.

Further advantages of the process of the present invention will appear hereinafter.

DETAILED DESCRIPTION

In accordance with the process of the present invention any material which can be separated by electrophoresis can be transferred. Thus, for example, both proteins and nucleic acids can be routinely electroblotted and irreversibly absorbed on a membrane. Sugars and other charged molecules can be used with appropriate trapping transfer membranes or molecular sieves. Naturally, any of the conventional gels can be employed, such as agarose and polyacrylamide gels, combinations of materials, and the like. Also, DNA hybridization probes, antibodies, organics or inorganics can be transferred into the gel or onto the membrane. In the case of transfer to the gel if their size and charge is such that they can enter the gel more rapidly than the larger DNA or protein migrates out, the process of the present invention can be used to add or subtract, wash, etc., right on the gel. The rapidity of the transfer of the instant process makes it a practical approach to developing a diagnostic system. For example, the present process allows rapid secondary saturation of sites on blot membranes with non-homologous DNA by electroblotting solutions contained in absorbant material saturated with reactant placed contiguous to the blot membranes. Also this allows washing of excess materials from blot membranes using absorbant materials saturated with buffer. In addition, this allows instantaneous mixing of probes to blotted biological materials and after an adequate hybridization period (generally twelve hours) could be followed by washing of excess material out of membranes. The present process also allows mixing of reactants to accomplish secondary reactions of organics to identify locus of probe, e.g., avidin plus chromophore binding to biotin labelled probe. Still further, the present process allows double reactions to identify probes of utility for screening. One can use large DNA on gel, probe on blot membrane, secondary saturated with non-homologous DNA. One can then transfer DNA to blot to show homologous DNA probe. Also, the present process can react an enzyme on the blot with substrates. Still further the present process allows the changing of ionic strength within a thin gel or membrane or between solutions passed between electrodes and separated by a semi-permeable membrane, and can lend itself to electrodialysis systems. Other applications will be apparent to those skilled in the art.

The electrophoretically resolved material in the gelatin sheet is placed in contacting relationship with an immobilizing material. Any suitable immobilizing material can be used, such as membranes, papers, nylon, nitrocellulose, diazobenzyloxymethyl (DBM) paper, diazophenylthioether (DPT) paper, and the like.

It is an advantage of the present invention that any suitable conductive sheet compatible with the process may be used as electrode material. Thus, while carbon electrodes are preferred, one may also use such materials as brass, copper and stainless steel. The electrodes may also be plated with appropriate coatings such as, but not limited to, nickel, chrome or platinum. Also, the electrodes may be designed so as to be disposable.

Although the process of the present invention may be designed to operate extremely quickly so that no visible gas bubbles are generated at the electrodes, it is of course contemplated in accordance with the present invention to provide appropriate paths and holes built-in for release of gases. Thus, one may utilize fine screens of copper, porous carbon, aluminum or other electrical grid with supporting backing. Also, one can place porous conductive pads, pre-saturated with buffer, under each electrode as an alternative method of dissipating a small quantity of bubbles.

Naturally, the electrode material must be able to conduct the high amperages experienced (as high as 20 plus amps) without heat-up. The copper electrode assembly lends itself to cooling of the electrodes. Also, all materials used in the system, except the electrodes and connecting wire, must be non-conductive.

In the preferred embodiment, the gel-membrane combination is sandwiched between the electrodes in contacting relationship with preferably a small amount of buffer applied to the interface between the electrodes and the gel-membrane combination to insure good conductivity. Any of the conventional non-reactive, electrically conductive buffers may be readily employed as is well known in the art. Naturally, the electrodes must be in electrical contact; however, it is not necessary to submerge the gel-membrane combination in buffer which represents an advantage of the process of the present invention. If desired, however, one can maintain the electrodes in non-contacting relationship with the gel-membrane combination and submerge the assembly in buffer. This is not as efficient an operation and is less preferred since the buffer layer will then also conduct current, increasing the amperage required.

The rate of pattern transfer is roughly proportional to the magnitude of the applied voltage. For applications requiring low voltage (longer running times) the electrodes may be made of porous material or have small holes or grooves in their surfaces to facilitate escape of gas bubbles.

With the classic platinum grid system the voltage cannot exceed 80–100 V (500 Ma) or the solution will heat up causing the gel to melt. Cooled systems allow slightly greater voltages. In accordance with the process of the present invention with for example carbon electrodes, the voltages are much less, e.g., 5–25 V for a 1/16" to ⅛" gel; however, the amperage (dependent on the gel-buffer salt concentration) is much greater, e.g., up to 12 amps at 5–25 V for a 2"×3" gel. It is feasible to go to still greater voltage and amperage for very short pulses. Thus, it can be seen that in accordance with the process of the present invention the current requirements can be widely varied and are not particularly critical. In the dry system the amperage is defined by the conductance of the gel and in the wet system by the conductance of the gel plus buffer confined between the electrodes; however, in the conventional platinum electrode system the amperage is determined by the gel plus the large volume of buffer in the space between the electrodes.

In the dry system the gel is the only conductant medium. Therefore, the salt concentration in the gel greatly affects the current passage. For example, using $\frac{1}{8}$" thick, 2"×3" gels of weak ionic strength (0.05 M tris-HCl acetate, pH 8.0), blotting is achieved at approximately 4 to 8 minutes at 10 V and 2 amps (25 watts). In addition, under conditions where DNA gel is fixed (denatured in 1.5 M NaCL, 0.5 M NaOH and then neutralized in 1 M, pH 8.0 Tris-HCl, 1.5 M NaCl), fairly complete blotting was achieved at:

(1) 240 seconds at 5 amps, approximately 4 V and 20 Watts;
(2) 120 seconds at 8 amps, approximately 4.5 V and 36 Watts;
(3) 30 seconds at 12 amps, approximately 6 V and 72 Watts.

Clearly, additional speed of transfer can be achieved with less heat and even less electrode bubbles using a larger power supply and greater amperages. For example, if desired, good blotting can be obtained at less than one second at 1000 Watts.

As indicated above, it is an advantage of the present invention that the process can be operated in a horizontal or vertical mode as desired. Obviously, the horizontal mode with a stable platform is easier to load and permits electroblotting of very soft gels which would tend to slide or collapse in a vertical system. Also, the horizontal mode lends itself to a continuous, on-line process leading to an automated system.

The process of the present invention will be more readily understood from the following additional examples.

EXAMPLES

In these examples $\frac{1}{8}$" and $\frac{1}{4}$" thick carbon electrodes were employed having dimensions of $4\frac{1}{2}$"×$5\frac{1}{2}$". Channels and drill holes were prepared with a $\frac{1}{4}$" grid pattern and 1/64" gas escape holes at $\frac{3}{4}$" intervals. The gel-membrane combination was sandwiched between the electrodes in contacting relationship using a thin layer of non-conducting tape around the perimeter to prevent contact between the electrodes.

To demonstrate transfer of electrophoretically resolved material, DNA was employed in the following manner. First 1 microgram of DNA was predigested to known fragment sizes, labeled, stopped and diluted to 200 microliters with loading buffer. The resultant material was loaded evenly across a 2"×3" gel in one band.

For the time studies nylon membrane material was cut into strips and laid across the gel which itself was lying on the cathodic electrode. The anodic electrode was placed on top of the strips and gel and the sandwich compressed gently in place. At times strips of the membrane were removed.

At the end of the experiment strips and remaining gel were placed against film. After incubation at −20° C. for exposure times to optimize band visualization, the films were developed. Subsequently, the strips were counted in a scintillation counter to give an approximate count.

In the first experiments the anodic electrode (scratched grid side up) was covered with the gel. The charged transfer membrane was placed on top of the gel and the cathodic electrode (scratched grid side down) was placed on top of the membrane. The resulting sandwich was lightly clamped together and placed in a chamber containing buffer solution. Electrical cords were connected and 12 Volts DC was applied for a period of eight minutes. At the completion of the runs the sandwich was drained and opened and the transfer membrane was placed against X-ray film to show the electroblot pattern. The results were good transfer to the membrane with excellent pattern definition and resolution.

The following experiment utilized the procedure set out above without immersion in a buffer solution. In this experiment the inside of the electrodes were wetted with a small amount of buffer to insure good conductance. The transfer to the membrane was complete within 80 seconds with excellent pattern definition and resolution. In fact, it was possible to visualize all DNA bands within 20 seconds.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed is:

1. A method for rapid molecular transfer without immersion in a buffer solution which comprises: providing an electrophoretically resolved material in a gelatin sheet; placing said gelatin sheet in contacting relationship with an immobilizing material to form a sheet-material combination; sandwiching said sheet-material combination between two plate electrodes in direct face-to-face relationship therewith to form an assembly; and applying electric current to said electrodes to provide transfer of electrophoretically resolved material to the immobilizing material without immersion in a buffer solution and in short periods of time.

2. The method of claim 1 wherein said immobilizing material is paper.

3. The method of claim 1 wherein said immobilizing material is nylon.

4. The method of claim 1 wherein said sheet-material combination is in contacting relationship with said plate electrodes.

5. The method of claim 1 wherein a small amount of a non-reactive, conductive buffer solution is placed between the plate electrodes and sheet-material combination.

6. The method of claim 1 wherein said assembly is horizontally disposed.

7. The method of claim 1 wherein said plate electrodes are flat plates.

8. The method of claim 7 wherein said plate electrodes are flat carbon plates.

9. The method of claim 1 wherein said plate electrodes include holes therein for release of gases.

10. The method of claim 1 wherein said plate electrodes include grooves therein for release of gases.

11. The method of claim 1 wherein said plate electrodes are able to conduct amperages as high as 20 amps without heat-up.

12. The method of claim 1 wherein said assembly is placed under compression.

* * * * *